United States Patent [19]
Neff et al.

[11] Patent Number: 5,925,736
[45] Date of Patent: Jul. 20, 1999

[54] COLLAGEN-BASED METHODS AND FORMULATIONS FOR THE TREATMENT OF ARTHRITIS

[75] Inventors: Thomas Neff, Laguna Beach, Calif.; George Martin, Bethesda; Karl A. Piez, Chevy Chase, both of Md.; Taina Pihlajaniemi, Oulunsalo; Kari I. Kivirikko, Oulu, both of Finland

[73] Assignee: FibroGen, Inc., South San Francisco, Calif.

[21] Appl. No.: 09/085,363

[22] Filed: May 27, 1998

Related U.S. Application Data

[60] Continuation-in-part of application No. 08/587,068, Jan. 11, 1996., abandoned, which is a continuation-in-part of application No. 08/370,388, Jan. 10, 1995., abandoned

[51] Int. Cl.⁶ .......................... A61K 38/17; A61K 38/00
[52] U.S. Cl. .......................... 530/356; 530/361; 530/868; 514/2; 514/8; 514/21; 514/885; 424/184.1
[58] Field of Search ................................ 530/356, 361, 530/868; 514/2, 8, 21, 885; 424/184.1

[56] References Cited

U.S. PATENT DOCUMENTS 5,399,347    3/1995   Trentham et al. .................... 424/184.1

OTHER PUBLICATIONS

"Fundamental Immunology," (Paul, W. ed.) 2d Ed., pp. 571–586, 600–605, 822–825 & 906, 1994.

Aichele et al., "Peptide–induced T–cell tolderance to prevent autoimmune diabetes in a transgenic mouse model" *Proc. Nat. Acad. Sci. U.S.A.* vol. 91, pp. 444–448 (1994).

Ayad et al., "Bovine Cartilage Types V and IX Collagens," *Biochem. J.* 262:753–761 (1989).

Boissier, et al., "Arthritogenicity of Minor Cartilage Collagens (Types IX and XI) In Mice," *Arthritis & Rheumatism* 33(1):1–8 (1990).

Charriere, et al., "Antibodies to Types I, II, IX and XI Collagen in the Serum of Patients with Rheumatic Diseases," *Arthritis & Rheumatism* 31(3):325–32 (1988).

Chiocchia et al., "T Cell Regulation of Collagen–Induced Arthritis in Mice," *J. Immunol.* 145(2):519–25 (1990).

Cremer et al., "Type XI Collagen–Induced Arthritis in the Lewis Rat," *J. Immunol.* 153(2):824–32, 1992.

Diab, "The Role of Type IX Collagen in Osteoarthritis and Rheumatoid Arthritis," *Orthop. Rev.* 22(2):165–70 (1993).

Duance et al., "Isolation and Characterization of the Precursor of Type M Collagen," *Biochem. J.* 221:885–889 (1984).

Grant et al., "The Structure and Synthesis of Cartilage Collagens," *The Control of Tissue Damage*, (Glauert A. ed.), pp. 3–28 (1988).

Krane et al., "Clinical Implications of Cartilage Metabolism in Arthritis," *Eur. J. Rheumatol. Inflamm.* 10(1):4–9 (1990).

Liu et al., "Chemical Abstracts," vol. 115, p. 679, Ref. No. 133025b (1991) (Oral Microbiol. Immunol. 6(1)1–5, (1991)).

Miller et al., "Preparation and Characterization of the Different Types of Collagen," *Methods in Enz.* 82:33–64 (1982).

Morgan et al., "Antibodies to Type II and XI Collagens: Evidence for the Formation of Antigen Specific as Well as Cross Reacting Antibodies in Patients with Rheumatoid Arthritis," *Ann. Rheum. Dis.* 47(12):1008–13 (1988).

Novotna, et al. "Contribution to the Mode of Action of Univalent Gold," *J. Rheumatol.* 50(2):93–98 (1991).

Thompson, et al. "Suppression of Collagen Induced Arthritis by Oral Administration of Type II Collagen: Changes in Immune and Arthritic Responses Mediated by Active Peripheral Suppression," *Autoimmunity* 16:189–199 (1993).

Trentham, et al. "Effects of Oral Administration of Type II Collagen on Rheumatoid Arthritis," *Science* 261:1727–1730 (1993).

Tish et al. "Antigen–specific immunotherapy: Is it a real possibility to combat T–cell–mediated autoimmunity?," *Proc. Natl. Acad. Sci. U.S.A.*, 91:437–438 (1994).

*Primary Examiner*—Cecilia J. Tsang
*Assistant Examiner*—Adbel A. Mohamed
*Attorney, Agent, or Firm*—Pennie & Edmonds LLP

[57] ABSTRACT

The invention provides novel methods and compositions for the treatment of immune system-mediated arthritis, including rheumatoid arthritis. The subject compositions comprise one or more different types of collagen or collagen derivatives and a mucosa binding structure. Specific combinations of collagen and/or collagen derivatives may be used to treat specific types of arthritis. The collagen(s) and/or collagen(s) derivatives used in the subject compositions may be either obtained from natural sources or produced by recombinant genetic engineering techniques by chemical modification. Another aspect of the invention is to provide methods for treating various types of arthritis by administering an effective amount of the subject collagen-containing compositions. The methods of the invention involve the oral administration of a collagen or collagens found in a specific tissue, e.g., cartilage, so as to induce the suppression (immunological tolerance) of inflammation against the tissue from which the collagen is found to occur in nature. The methods of the invention include the administration of the subject collagen(s) and/or collagen derivative(s) containing compositions into the intestines so as to induce immune tolerance, e.g., oral administration.

14 Claims, No Drawings

COLLAGEN-BASED METHODS AND FORMULATIONS FOR THE TREATMENT OF ARTHRITIS

RELATED APPLICATIONS

This application is a continuation-in-part of U.S. Ser. No. 08/587,068, filed on Jan. 11, 1996, which is a continuation-in-part of U.S. application Ser. No. 08/370,388, filed on Jan. 10, 1995 now both abandoned.

FIELD OF THE INVENTION

The invention is in the field of autoimmune disease, in particular arthritis, and treatments thereof employing collagen and/or derivatives.

BACKGROUND OF THE INVENTION

While the immune system is essential for fighting off infections, the immune response to infections (foreign antigens) and the immune response to molecules produced in the body (autologous antigens) may result in numerous diseases, i.e., immune system-mediated diseases. Immune system-mediated diseases may be either B cell-mediated (i.e., antibody-mediated) or T cell-mediated. Additionally, immune system-mediated diseases may be caused by immune complexes formed between antibodies and antigens (either foreign or autologous). Many immune system-mediated diseases involve an undesirable inflammatory response, e.g., diseases which include rheumatoid arthritis, chronic hepatitis, Crohn's Disease, psoriasis, vasculitis, and the like.

Existing therapies for immune system-mediated diseases, particularly immune system-mediated diseases resulting in an undesirable inflammatory response, such as rheumatoid arthritis, are inadequate. Most immune system-mediated diseases are chronic conditions which require the prolonged administration of drugs. Accordingly, it is important to employ relatively non-toxic drugs. However, many compounds used for the treatment of autoimmune diseases, e.g., steroids and non-steroidal anti-inflammatory compounds, have significant toxic side effects that become apparent after long-term use. Additionally, immunosuppressive drugs have been used to treat autoimmune responses. Such immunosuppressive drugs, e.g., cyclosporin A and azathioprine, are relatively non-specific and have the adverse effect of weakening the entire immune system, thereby leaving a patient susceptible to infectious disease.

The oral administration of compounds has been shown to induce immune tolerance with respect to the ingested compound and compounds structurally related to the ingested compound. It has been suggested that the phenomenon of oral tolerance induction be adapted as a method of treating autoimmune disease. PCT publication WO 95/10301 describes the use of oral ingested cholera toxin conjugates to decrease a delayed hypersensitivity reaction and control experimental autoimmune encephalitis in mouse models.

In view of the shortcomings of existing techniques for treating chronic immune system-mediated diseases, it is of interest to provide new methods and compositions for the treatment of immune system-mediated diseases, including rheumatoid arthritis. Methods described herein employ one or more collagens and/or collagen derivatives so as to reduce or eliminate an immune response that is important for the pathogenesis of rheumatoid arthritis. The methods and formulations are designed to induce tolerance to antigens involved in the disease process.

SUMMARY OF THE INVENTION

The subject invention provides novel methods and compositions for the treatment of arthritis, in particular rheumatoid arthritis. The subject compositions comprise one or more different types of collagen or collagen derivatives. Specific combinations of collagen and/or collagen derivatives may be used to treat arthritis, in particular rheumatoid arthritis. The collagen(s) and/or collagen(s) derivatives used in the subject compositions may be either obtained from natural sources or produced by recombinant genetic engineering techniques.

Another aspect of the invention is to provide methods for treating arthritis by administering an effective amount of the subject collagen-containing compositions. The methods of the invention include the administration of the subject collagen(s) and/or collagen derivative(s) containing compositions into the intestine so as to induce immune tolerance, i.e., oral administration.

Another aspect of the invention is to provide the subject collagen and/or collagen derivative containing compositions formulated for administration to a patient. Preferred formulations of the invention are designed for the release of collagen(s) and/or collagen derivatives in the intestine so as to contact intestinal lymphoid tissue. In a preferred embodiment of the invention the subject compositions are formulated for oral administration.

Another aspect of the invention is to provide collagen derivatives that comprise at least one tolerance inducing epitope, and preferably a plurality of tolerance inducing epitopes. Such collagen derivatives may comprise a plurality of different collagen-derived tolerance inducing epitopes and are referred to herein as tolerance epitope polypeptides. Tolerance epitope polypeptides may also comprise amino acid resolve sequences derived from non-collagenous proteins.

Another aspect of the invention is to provide mucosa binding collagen conjugates for treating arthritis. The mucosa binding collagen conjugates of the invention comprise one or more collagen molecules linked to a mucosa binding molecule. A variety of different collagen and/or collagen derivatives may be used as the collagen component of the mucosa binding collagen conjugates of the invention. Suitable mucosa binding components include mucosa binding structures derived from bacterial toxins, bacterial fimbriae, viral attachment proteins, and plant lectins. Particularly preferred mucosa binding components are the β subunit of cholera toxin and the β subunit of E. coli heat labile enterotoxin.

Another aspect of the invention is to provide methods of treating arthritis by administering an effective amount of a mucosa binding collagen conjugate. Yet another aspect of the invention is to provide formulations for use in the treatment of arthritis, in particular rheumatoid arthritis, wherein the formulation comprises a mucosa binding collagen conjugate of the invention. Preferably, the formulations are adapted for oral administration.

DESCRIPTION OF THE SPECIFIC EMBODIMENTS

The invention involves the use of one or more different collagens and/or collagen derivatives to induce oral tolerance in a specific population of immune cells so as to provide a method of treating arthritis, in particular rheumatoid arthritis. Methods of using various collagens and/or collagen derivatives to treat arthritis and compositions for use in such methods are provided herein. The methods of the invention involve the oral administration of a collagen or collagens found in a specific tissue, i.e., cartilage, so as to induce the suppression (immunological tolerance) of inflammation against the tissue (or tissues) from which the collagen is found to occur in nature. Collagen (and collagen derivative) containing compositions for use in such methods are also provided. The invention also provides many different types of mucosa binding collagen conjugates and methods for their use in treating arthritis.

One aspect of the invention is to use minor collagens, i.e., comparatively rare collagens found to be naturally associated with major collagens, to induce immune tolerance so as to reduce the severity of an undesirable immune response, thereby providing the basis of a treatment of arthritis, in particular rheumatoid arthritis; however, the invention also provides for the use of major collagens to induce immune tolerance. Cartilage contains diverse species of collagen that provide the major extracellular scaffolding for the surrounding tissue. Data has been found to suggest that type II collagen, a major collagen, may have the capacity to suppress inflammation in cartilage. The subject invention is based, in part, upon the realization that minor collagen(s) naturally found to occur in combination with major collagen (s) may be important in inducing immune tolerance useful in treating arthritis, in particular rheumatoid arthritis. Accordingly, one aspect of the invention is to use minor collagens, either alone or in combination with major collagens, to induce immune tolerance that results in amelioration of the disease process in arthritis, e.g., rheumatoid arthritis.

The subject invention provides a variety of collagen and collagen derivative containing compositions. Different combinations may be employed dependent on the specific type of arthritis to be treated. Numerous different types of collagen are known to the person of ordinary skill in the art. At present, nineteen different types of collagen have been discovered. A detailed description of the structure and the biological functions of the various different types of naturally occurring collagens can be found, among other places, in Ayad et al., *The Extracellular Matrix Facts Book*, Academic Press, San Diego, Calif.; Burgeson, R. E., and Nimmi, "Collagen types: Molecular Structure and Tissue Distribution," *Clin. Orthop.*, 282:250–272 (1992); Kielty, C. M., et al., "The Collagen Family: Structure, Assembly And Organization In The Extracellular Matrix." In *Connective Tissue And Its Heritable Disorders, Molecular Genetics, And Medical Aspects*, Royce, P. M. and Steinmann, B., Eds., Wiley-Liss, N.Y., pp. 103–147 (1993).

Type I collagen is the major fibrillar collagen of bone and skin. Type I collagen is a heterotrimeric molecule comprising two α1(I) chains and one α2(I) chain. Details on preparing purified type I collagen can be found, among other places, in Miller, E. J., and Rhodes, R. K., *Methods In Enzymology*, 82:33–64 (1982), Academic Press.

Type II collagen is a homotrimeric collagen comprising three identical α1(II) chains. Purified type II collagen may be prepared by, among other methods, the procedure described in Miller, E. J., and Rhodes, R.K. *Methods In Enzymology*, 82:33–64 (1982), Academic Press.

Type III collagen is a major fibrillar collagen found in skin and vascular tissues. Type III collagen is a homotrimeric collagen comprising three identical α1(III) chains. Methods for producing type III collagen can be found in, among other places, Byers, et al., *Biochemistry*, 13:5243–5248 (1974) and Miller E. J. and Miller, R. K., *Methods in Enzymology*, 82:33–64 (1982), Academic Press.

Type IV collagen is found in basement membranes in the form of a sheet rather than fibrils. Type IV collagen molecules are composed of three different alpha chains derived from six different genes, i.e., type IV collagen comprises three of α1(IV), α2(IV), α3(IV), α4(IV), α5(IV), and α6(IV) chains. The particulars are expressed in a tissue-specific manner. Type IV collagen may be purified by, among other methods, the procedures described in Furuto et al., D. K., and Miller, E. J., *Methods in Enzymology*, 144:41–61 (1987), Academic Press.

Type V collagen is a fibrillar collagen found in bones, tendon, cornea, skin, and blood vessels. Type V collagen exists in both homotrimeric and heterotrimeric forms. One type of type V collagen is a heterotrimer of two α1(V) chains and one α2(V) chain. Another type of type V collagen is a heterotrimer of α1(V), α2(V), and α3(V) chains. Yet another type of type V collagen is a homotrimer of three identical α1(V) chains. Methods for purifying type V collagen can be found, among other places, in Elstrow, S. F., and Weiss, J. B., *Collagen Rel. Res.*, 3:181–193 (1983) and Abedin, et al., *Biosci. Rep.*, 2:493–502 (1982).

Type VI collagen has a small collagenous triple helical region and a large non-collagenous remainder portion. Type VI collagen is found in many connective tissues. Type VI collagen is a heterotrimer comprising α1(VI), α2(VI), and α3(VI) chains. Descriptions of how to purify type IV collagen can be found, among other places, in Wu, et al., *Biochem. J.*, 248:373–381 (1987), and Kielty, et al., *J. Cell Sci.*, 99:797–807.

Type VII collagen is a fibrillar collagen found in particular epithelial tissues. Type VII collagen is a homotrimeric molecule of three α1(VII) chains. Descriptions of how to purify type VII collagen can be found in, among other places, Lundstrom, et al., *J. Biol. Chem.*, 261:9042–9048 (1986), and Bentz, et al., *Proc. Natl. Acad. Sci. U.S.A.*, 80:3168–3172 (1983).

Type VIII collagen can be found in Descemet's membrane in the cornea. Type VIII collagen is a heterotrimer comprising two α1(VIII) chains and one α2(VIII) chain. Methods for the purification of type VIII collagen can be found, among other places, in Benya and Badilla, *J. Biol. Chem.*, 261:4160–4169 (1986), and Kapoor, et al., *Biochemistry*, 25:3930–3937 (1986).

Type IX collagen is a fibril associated collagen which can be found in cartilage and vitreous humor. Type IX collagen is a heterotrimeric molecule comprising α1(IX), α2(IX), and α3 (IX) chains. Procedures for purifying type IX collagen can be found, among other places, in Duance, et al., *Biochem., J.*, 221:885–889 (1984), Ayad et al., *Biochem. J.*, 262:753–761 (1989), Grant, et al., *The Control of Tissue Damage*, Glauert, A. M., Ed., El Sevier, Amsterdam, pp. 3–28 (1988).

Type X collagen is a homotrimeric compound of three identical α1(x) chains. Type X collagen has been isolated from, among other tissues, hypertrophic cartilage found in growth plates.

Type XI collagen can be found in cartilaginous tissues associated with type II and type IX collagens, as well as in other locations in the body. Type XI collagen is a heterotrimeric molecule comprising α1(XI), α2(XI), and α3(XI) chains. Methods for purifying type XI collagen can be found, among other places, in Grant et al., *In The Control of Tissue Damage*, Glauert, A. M., Ed., El Sevier, Amsterdam, pp. 3–28 (1988).

Type XII collagen is a fibril associated collagen found primarily associated with Type I collagen. Type XII collagen is a homotrimeric molecule comprising three α1(XII) chains. Methods for purifying type XII collagen and variants thereof can be found, among other places, in Dublet et al., *J. Biol. Chem.,* 264:13150–13156 (1989), Lundstrum et al., *J. Biol. Chem.,* 267:20087–20092 (1992), Watt et al., *J. Biol. Chem.,* 267:20093–20099 (1992).

Type XIII collagen is a non-fibrillar collagen found, among other places, in skin, intestine, bone, cartilage, and striated muscle. A detailed description of type XIII collagen may be found, among other places, in Juvonen, et al., *J. Biol. Chem.,* 267:24700–24707 (1992).

Type XIV collagen is a fibril associated collagen. Type XIV collagen is a homotrimeric molecule comprising three α1(XIV) chains. Methods for isolating type XIV collagen can be found, among other places, in Aubert-Foucher, et al., *J. Biol. Chem.,* 266:19759–19764 (1992) and Watt, et al., *J. Biol. Chem.,* 267:20093–20099 (1992).

Type XV collagen is homologous in structure to type XVIII collagen. Information about the structure and isolation of type XV collagen can be found, among other places, in Myers et al., *Proc. Natl. Aca. Sci. USA,* 89:10144–10148 (1992), Huebner et al., *Genomics,* 14:220–224 (1992), Kivirikko et al., *J. Biol. Chem.,* 269:4773–4779 (1994), and Muragaki, *J. Biol. Chem.,* 264:4042–4046 (1994).

Type XVII collagen is a fibril associated collagen, found in skin, lung fibroblasts, keratinocytes, and elsewhere. Information on the structure of type XVI collagen and the gene encoding type XVI can be found, among elsewhere, in Pan et al., *Proc. Natl. Acad. Sci, U.S.A.,* 1989:6565–6569 (1992), and Yamaguchi, et al., *J. Biochem.,* 112:856–863 (1992).

Type XVIII collagen is homologous in structure to type XV collagen and can be isolated from the liver. Descriptions of the structures and isolation of type XVIII collagen can be found, among other places, in Rehn et al., *Proc. Natl. Acad. Sci USA,* 91:4234–4238 (1994), Oh et al., *Proc. Natl. Acad. Sci USA,* 91:4229–4233 (1994), Rehn et al., *J. Biol. Chem.,* 269:13924–13935 (1994), and Oh et al., *Genomics,* 19:994–999 (1994).

The above-collagen types may also be obtained by recombinant expression techniques, as described generally in U.S. Pat. No. 5,405,757, PCT-published patent applications WO 93/07889 and WO94/16570, and related patents and applications.

Another aspect of the invention is to provide mucosa binding collagen conjugates. The subject mucosa binding collagen conjugates comprise a collagen component and a mucosa binding component. The two components may be linked directly to one another or may be linked to one another through one or more intermediary linking molecules. Mucosa binding collagen conjugates may be used to treat arthritis, e.g., rheumatoid arthritis. The treatment is effected through the induction of immune tolerance to one or more epitopes on the collagen component of the mucosa binding collagen conjugates.

The collagen component of the subject mucosa binding collagen conjugates may comprise one or more collagen or collagen derivative molecules. The collagen molecules of the collagen component of the mucosa binding collagen conjugates may be the same or different from one another. The collagen/collagen derivative molecules of the collagen component may be linked to one another, either directly or through linker intermediates. Alternatively, the collagen/collagen derivatives of the collagen component are not necessarily linked to each other, but may be linked directly to the mucosa binding component of the subject mucosa binding collagen conjugates.

The mucosa binding component comprises one or more molecules capable of specifically binding to the mucosa cells of a patient for treatment. A variety of different molecules may serve as the mucosa binding component. These mucosa binding molecules may be derived from the mucosa binding structures of bacterial toxins, bacterial fimbriae, viral attachment proteins and plant lectins. The use of mucosa binding structures from bacterial toxins is preferred. Particularly preferred are the β subunits of cholera toxin and the β subunits of the heat-labile enterotoxin of *E. coli*. The β subunits of cholera toxin and the β subunits of the heat-labile enterotoxin of *E. coli* have the property of specifically binding to ganglioside $GM_1$, in mucosal cells. When toxins are used as mucosa binding structures, the toxin is preferably modified so as to significantly remove and destroy the cytotoxic properties of the toxin. Inactivation of cytotoxic properties my be accomplished in a number of ways well known to the person of ordinary skill the art including, for example, denaturation, mutation, and the like. Other molecules that specifically bind to ganglioside $GM_1$, may be used as the mucosa binding component of the mucosa binding collagen conjugates of the invention. The mucosa binding molecules may be covalently joined to one another, either directly or indirectly, by means of an intermediary linker molecule(s). Alternatively, the mucosa binding molecules that form the mucosa binding component may associate with one another by means of intermolecular attractive forces. For example, the β subunits of cholera toxin form a 5 molecule "ring" structure when allowed to associate. Examples of suitable toxin molecules include subunits S2, S3, S4 and/or S5 of *Bordatella pertussis* toxin, diphtheria toxin, diphtheria toxin β fragment, shiga toxin, shiga-like toxins, shiga toxin β subunit, shiga-like toxin β subunit, cholera toxin, and *E. coli* heat-labile toxin. Examples of suitable bacterial fimbriae include *E. coli* K88, K99, 987P, F41, CFA/I, CFA/II, (CS1, CS2 and/or CS3), CFA/IV (CS4, CS5 and/or CS6), *P. fimbriae, Vibrio cholera* toxin co-regulated pili (TCP), mucus sensitive hemagglutinin (MSHA), fucose-sensitive hemagglutinin (FSITH), *B. pertussis* filamentous hemagglutinin and the like. Examples of suitable viral attachment proteins include Influenza hemagglutinin and Sendai Virus hemagglutinin. Examples of suitable lectins include both plant lectins and animal lectins, soluble lactose-binding lectins, selecting, collecting, helix pomatin hemagglutinin, concanavalin A, wheat-germ agglutinin, phytohemagglutinin, aurin and ricin. Immunoglobins that are specific for mucosal cell antigens may also be used as mucosal binding components.

The separate collagen component and mucosa binding component of the mucosa binding conjugates may be linked to one another by a variety of means. The two components may be coupled together by means of chemical cross-linking agents such as N-succinimidyl (3-(2-pyridyl-dithio)) propionate, dimethyl-3,3'-dithiobispropionimidate, 2-iminothiolane, N-succinimidyl-(4 azidophenyl)-1, 3-dithioprionate, ethyl-4- azidophenyl-1, 4-dithiobutyrimidate, diethyl malonimidate, 2-iminothiolane, N,N'-p- phenylenedimaleimide, and the like. Alternatively, the mucosa binding collagen conjugates of the invention may be joined by single polypeptides that are fusion proteins that link the mucosa binding collagen conjugate between the collagen component and the mucosa binding molecule component. These fusion proteins may be produced by conventional in vitro genetic engineering techniques. Another aspect of the invention is to provide polynucleotide sequences encoding mucosa binding collagen conjugate fusion proteins. Yet another aspect of the invention is to provide host cells for the recombinant production of mucosa binding collagen conjugate fusion proteins.

The mucosa binding molecule components may be obtained by purifying them from their naturally occurring source organism. Alternatively, the mucosa binding molecule components may be produced by recombinant DNA techniques. Methods of purifying mucosa binding molecules, or alternatively, recombinantly producing such molecules suitable for use in the invention are well known to the person of ordinary skill in the art. For example, the recombinant production of cholera toxin β subunit has been described in Sanchez and Holmgren, *Proc. Natl. Acad. Sci. (USA)*, 86:481–485 (1989) and production of the β subunit of *E. coli* heat labile enterotoxin has been described in Hirst et al., *Proc. Natl. Acad. Sci. (USA),* 81:7752–7756 (1984).

The compositions of the invention comprise one or more purified collagens and/or collagen derivatives. The subject compositions comprising specific combinations of collagens and/or collagen(s) derivatives are provided. TABLE 1 sets forth a list of collagen types (indicated by Arabic numeral rather than Roman numerals) that may be used to treat arthritis, e.g., rheumatoid arthritis. Each of the collagen types is listed may be useful alone or in a composition combining one or more suitable collagen molecules. Additional minor types may be identified to involved in certain types of arthritis or in particular certain types of rheumatoid arthritis or its auxiliary conditions and may be employed accordingly. For example, by reference to TABLE 1, it can be seen that many types of arthritis, e.g., rheumatoid arthritis, may be treated by compositions comprising type I collagen, type II collagen, type III collagen, type V collagen, type VI collagen, type IX collagen, type X collagen, type XI collagen, type XII collagen, type XIV collagen, or any combination thereof comprising two or more of the collagens indicated as being suitable for the treatment of types of arthritis, e.g., rheumatoid arthritis. Thus, it can be seen that the invention provides compositions for the treatment of arthritis, e.g., rheumatoid arthritis comprising at least one compound selected from the group consisting of type I collagen, type II collagen, type III collagen, type V collagen, type VI collagen, type IX collagen, type X collagen, type XI collagen, type XII collagen and type IV collagen. Collagen derivatives corresponding to a given collagen type may also be used in addition to or in place of a specific collagen type indicated in the compositions of TABLE 1. Thus, for example, a composition for the treatment of arthritis, as indicated in TABLE 1, may comprise type II collagen, a type II collagen derivative, multiple different type II collagen derivatives, or a mixture of type II collagen and type II collagen derivatives.

In a preferred embodiment of the invention for treating types of arthritis, the subject compositions comprise type IX collagen and/or type IX collagen derivatives thereof, either with or without type II collagen and/or derivatives of type II collagen. In another embodiment, the invention provides compositions that comprise type XI collagen and/or derivatives thereof, either with or without type II collagen and/or derivatives thereof. In another preferred embodiment of the invention for treating rheumatoid arthritis, the invention consists of compositions comprising type IX collagen and/or derivatives thereof and type XI collagen, either with or without type II collagen and/or derivatives thereof. In another preferred embodiment of the invention for treating rheumatoid arthritis, the subject compositions comprise type II collagen derivatives.

TABLE 1

TABLE OF COLLAGEN TYPES AND INDICATIONS

| | COLLAGEN TYPE | | | | | | | | | |
|---|---|---|---|---|---|---|---|---|---|---|
| INDICATION | 01 | 02 | 03 | 05 | 06 | 09 | 10 | 11 | 12 | 14 |
| reactive arthritis | | X | | | | X | | X | | |
| rheumatoid arthritis (including juvenile rheumatoid arthritis) | X | X | X | X | X | X | X | X | X | X |

Purified collagens for use in the methods and compositions of the subject invention may be isolated from animal or human tissues; however, the use of human collagens in the subject compositions and methods is preferred when the subject to be treated is a human. In addition to obtaining collagens for use in the subject methods and compositions from natural sources, collagens for use in the methods and compositions of the invention may be produced by recombinant DNA technology. A description of how to produce type II collagen by recombinant DNA technology technique can be found, among other places, in PCT-published patent applications WO 93/07889 and WO094/16570, which are herein incorporated by reference. The recombinant production techniques described in these PCT publications may readily be adapted so as to produce many different types of collagens, human or otherwise. Preferably, human collagens produced by recombinant DNA technology are used in compositions of the invention. Recombinant DNA technology avoids ethical and economic problems associated with obtaining adequate quantities of human tissue.

In addition to employing collagen obtained directly from natural sources, the methods and compositions of the invention may comprise many different types of collagen derivatives. Collagen derivatives may vary from naturally occurring collagens in several respects. Collagen derivatives may be non-glycosylated or glycosylated differently than naturally-occurring collagens. Desired glycosylation patterns may be produced by a variety of methods, including direct chemical modification and enzymatically catalyzed glycosylation and deglycosylation reactions. Desired glycosylation patterns may also be produced by inhibiting or deleting enzymes necessary for producing the naturally-occurring glycosylation patterns found on collagens. Collagen derivatives having a glycosylation pattern that differs from a corresponding naturally-occurring collagen, but are otherwise essentially the same in structure (except for the amount of proline and/or lysine residues that have been hydroxylated) are referred to herein as "variably glycosylated collagens." Collagen derivatives also include various fragments of naturally-occurring collagens. Such collagen fragments may be produced by, among other methods, chemically or enzymatically cleaving one or more peptide bonds. Collagen derivatives may also contain one or more amino acid residue differences as compared with corresponding amino acid residue positions in a naturally-occurring collagen. Collagen derivatives containing such amino acid residue substitutions may be produced by a variety of methods including genetic engineering techniques and by in vitro peptide synthesis. Additional collagen derivatives may be produced by varying the amount of hydroxylysines and/or hydroxyprolines present in a given molecule, by the varied expression of lysine hydroxylases, and/or proline hydroxylases, wherein the hydroxylase genes (recombinant or otherwise) are also expressed in a host cell for the expression of recombinant collagen, or derivatives thereof. Collagen derivatives for use in the compositions and methods of the invention have the capacity to reduce the undesired immune reaction in the arthritis of interest when administered to a patient either alone or as part of a composition of the invention, including compositions comprising a plurality of collagen and/or collagen derivatives. Collagen derivatives suitable for use in those methods and compositions of the invention for the treatment of arthritis, e.g., rheumatoid arthritis, may be determined by employing in vitro tests of T cells from rheumatoid arthritis patients, wherein the tests could determine if a given collagen derivative can stimulate suppressor T cells, induce clonal anergy, or induce other forms of immune tolerance. Methods of measuring antigen tolerance induction are well known to persons of ordinary skill in the art and can be found, for example, in Paul, W. E., editor, *Fundamental Immunology*, 2nd Ed., Raven Press: N.Y. (1994).

A collagen molecule, collagen derivative or mucosa binding collagen conjugate suitable for use in the methods of the invention comprises at least one tolerance inducing epitope. The term "tolerance inducing epitope" as used herein refers to epitopes on collagen that have the property of inducing immune tolerance with respect to a pathogenic immune response in arthritis, e.g., rheumatoid arthritis, independent of other portions of the collagen molecule from which the "tolerance-inducing epitope" was derived. Individual collagen molecules may comprise one or more tolerance inducing epitopes. Additionally, the tolerance-inducing epitope or epitopes on a given collagen molecule may vary in accordance with the specific type of arthritis to be treated by the collagen.

The invention also provides for collagen derivatives consisting of amino acid residue sequences that comprise one or more collagen tolerance-inducing epitopes; such novel polypeptides are referred to herein as "tolerance epitope polypeptides." Tolerance epitope polypeptides may comprise a plurality of identical tolerance-inducing epitopes. Tolerance epitope polypeptides of the invention may also comprise one or more non-identical tolerance-inducing epitopes derived from the same or different collagen molecules. Embodiments of the subject tolerance epitope polypeptides include polypeptides in which the different epitopes are arranged in a regular repeating pattern and polypeptides in which the various tolerance-inducing epitopes are arranged randomly. Tolerance epitope polypeptides comprise a plurality of tolerance-inducing epitopes; while tolerance epitope polypeptides may be of virtually any size, the person of ordinary skill in the art will appreciate that certain technical problems arise in synthesizing and using very large polypeptides, e.g., solubility, stability, etc. Accordingly, the tolerance epitope polypeptides of the invention preferably comprise 500 tolerance inducing epitopes, more preferably in the range of 100 to 250 tolerance-inducing epitopes and still more preferably in the range of 50 to 100 tolerance-inducing epitopes. Tolerance-inducing epitopes may be glycosylated or non-glycosylated, depending upon whether the carbohydrate matrix is considered to be part of a tolerance- inducing epitope. Tolerance epitope polypeptides may be produced by conventional genetic engineering techniques such as those described, for example, in Goeddel *Gene Expression Technology, Methods in Enzymology Volume* 185, Academic Press (1991). Additionally, tolerance epitope polypeptides may comprise one or more non-collagen derived amino acid residue sequences, whereby the collagen derived tolerance-inducing epitope region on the tolerance epitope polypeptide serves as a carrier for the non-collagen derived amino acid sequence so that immune tolerance can also be induced against the non-collagen derived amino acid residue sequence. In other words, some embodiments of the subject tolerance epitope polypeptides are polypeptides that act as "carriers" for inducing immune tolerance against non-collagen proteins that may be involved in the pathogenesis of certain types of arthritis. For example, the subject invention provides tolerance epitope polypeptides that comprise regions of myelin basic protein that have been shown to be important in the development of the pathogenic immune response in multiple sclerosis.

Polynucleotide sequences encoding tolerance epitope polypeptides may be produced by, among other methods, in vitro polynucleotide synthesis and the manipulation of previously-isolated collagen-encoding polynucleotides.

Tolerance epitope polypeptides may comprise tolerance-inducing epitopes derived from collagen or collagens found in a specific tissue so as to induce the suppression (immunological tolerance) of inflammation against the tissue (or tissues) from which the collagen is found to occur in nature. Thus, for example, a tolerance epitope polypeptide comprising tolerance-inducing epitopes of type II, type IX, and type XI collagen may be used in place of (or in addition to) a mixture of type II, type IX, and type XI collagens.

Tolerance-inducing epitopes for a given collagen and a given type of arthritis may be readily determined by a person of ordinary skill in the art of immunology. For example, certain subpopulations of lymphocytes in a person wiring from (or likely to develop) a specific types of arthritis have receptors capable of binding tolerance inducing options, wherein a putative tolerance-inducing epitope may be obtained by making systematic deletions in a collagen molecule of interest.

Another aspect of the invention is to provide methods of treating arthritis. The terms "treatment" or "treating" as used herein with reference to a disease refer both to prophylaxis and to the amelioration of symptoms already present in an individual. It will be appreciated by the person of ordinary skill in the art that a treatment need not be completely effective in preventing the onset of a disease or in reducing the symptoms associated with the disease. Any reduction of the severity of symptoms, delay in the onset of symptoms, or delay in the progression of severity of symptoms is desirable to a patient. Persons at risk of developing arthritis, e.g., rheumatoid arthritis may be treated prophylactically based on any of a variety of factors suggesting the possible onset of various types of arthritis, e.g., family history, genetic markers, early symptoms, and the like.

The treatment methods of the subject invention comprise the step of administering an effective amount of a composition of the invention, e.g., collagens, collagen derivatives, or mucosa binding collagen conjugates. Preferred compositions for use in treating arthritis are provided in TABLE 1, as described in the preceding sections. In a preferred embodiment of the subject methods, the compositions administered to the subject comprise variably glycosylated collagens or mucosa binding collagen conjugates, wherein the collagen component comprises variably glycosylated collagen molecules. The compositions administered in the subject methods are administered so that the active components, i.e., collagens and/or collagen derivatives, contact the lymphoid tissue of the gut, e.g., Peyer's patches or other similar sites, so that immune tolerance is induced. Such administration may be effected by many possible methods through the use of formulations comprising the subjected compositions that are designed for oral administration, i.e., the active components are not destroyed or inactivated in the mouth, stomach, or other portions of the digestive system prior to contacting the appropriate gut lymphoid tissue. The treatment methods of the invention may also comprise the steps of administering additional pharmaceutical compounds for the treatment of arthritis, such as anti-inflammatory agents and the like.

The dosage at which the subject compositions are administered may vary within a wide range and will depend on various factors such as for example the severity of the inflammation, the age of the patient, etc., and may have to be individually adjusted. A possible range for the amount of collagen(s) and/or collagen(s) derivatives which may be administered per day may be in the range of from about 0.001 mg to about 200 mg. Preferably, the amount of collagen and/or collagen derivatives administered is low, thereby favoring the induction of immune tolerance by suppression rather than clonal anergy. The pharmaceutical compositions containing the collagen(s) and/or collagen(s) derivatives may suitably be formulated so that they provide doses within these ranges either as single dosage units or as multiple dosage units.

The optimal dosage of tolerance inducing compositions for use in the methods of the invention will vary in accordance with a number of factors. The terms "dosage" and "dose" as used herein, unless indicated otherwise, may refer not only to a single administration of a composition but may be used to refer to the total amount of a given pharmaceutical composition administered over a selected period of time and involving multiple individual administrations. Factors affecting the optimal dosage include the choice of collagen molecule or molecules (and/or collagen derivatives) administered to the patient, the specific mucosa binding molecules selected, the age of the patient, the severity of the disease, other diseases that may be present in the patient, inert components in the formulation, adjuvants, and the like. There may be considerable variation in the range of dosages that are effective in treating specific types of arthritis. Different dosages of the same pharmaceutical composition may produce the desired tolerance effect by different mechanisms. Although the operation of the invention is not dependent upon a particular theory of operation, the person of ordinary skill in the art will better understand the invention and provide additional embodiments by appreciating that there are believed to be two primary mechanisms by which oral tolerance is mediated. Oral tolerance may be mediated by active cellular suppression in which regulatory T cells suppress the activation and proliferation of lymphocytes specific for tolerized antigen. Another mechanism of oral tolerance induction is clonal anergy in which T lymphocytes having a suitable receptor are rendered unresponsive. Generally, active suppression tolerance is favored by "low" doses of a tolerizing antigen and clonal anergy is favored by comparatively "high" doses of the same tolerizing antigen. A review of the principles and techniques for oral tolerance induction can be found in Weiner et al., *Annual Review of Immunology:* 1994, 809–835, Annual Reviews.

The subject compositions may be formulated as pharmaceutical compositions so as to be adapted for certain types of administration to mucosal surfaces, e.g., oral, topical, and inhalation. The preferred form of formulation for oral administration is a form where the collagen and/or collagen derivatives in the composition come into contact with intestinal lymphoid tissue, e.g., Peyer's patches. Compositions of the invention may be administered topically, orally, intranasally, by injection or by inhalation in the form of a pharmaceutical composition comprising a collagen(s) and/or collagen(s) derivatives in the form of the original compound or optionally in the form of a pharmaceutically acceptable salt thereof, in association with a pharmaceutically acceptable carrier which may be a solid, semi-solid or liquid diluent or an ingestible capsule, and such preparations comprise a further aspect of the invention. The collagen(s) and/or collagen(s) derivatives and mucosa binding collagen conjugates may also be used with carrier material. As examples of pharmaceutical preparations may be mentioned tablets, drops such as nasal drops, preparations for topical application such as ointments, jellies, creams and suspensions, aerosols for inhalation, nasal spray, liposomes, etc. Usually the collagen(s) and/or collagen(s) derivatives will comprise between 0.05 and 99%, or between 0.1 and 99% by weight of the preparation, for example between 0.5 and 20% for preparations intended for injection and between 0.1 and 50% for preparations intended for oral administration.

To produce pharmaceutical preparations in this form of dosage units for oral application containing a compound of the invention, the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a CARBOWAX® or other polyethylene glycol waxes and are compressed to form tablets or cores for dragees. If dragees are required, the cores may be coated, for example, with concentrated sugar solutions which may contain gum arabic, talc and/or titanium dioxide, or alternatively with a film forming agent dissolved in easily volatile organic solvents or mixtures of organic solvents. Dyestuffs can be added to these coatings, for example, to distinguish between different contents of active substance. For the preparation of soft gelatine capsules consisting of gelatine and, for example, glycerol as a plasticizer, or similar closed capsules, the active substance may be admixed with a CARBOWAX® or a suitable oil (e.g. sesame oil, olive oil, or arachis oil). Hard gelatine capsules may contain granulates of the active substance with solid, pulverulent carriers such as lactose, saccharose, sorbitol, mannitol, starches (for example) potato starch, corn starch or amylopectin), cellulose derivatives or gelatine, and may also include magnesium stearate or stearic acid as lubricants.

The compositions of the invention may also be formulated so as to provide a sustained release. By using several layers of the active drug, separated by slowly dissolving coatings, sustained release tablets may be obtained. Another way of preparing sustained release tablets is to divide the dose of the active drug into granules with coatings of different thicknesses and compress the granules into tablets together with the carrier substance. The collagen(s) and/or collagen(s) derivatives and mucosa binding collagen conjugates may also be incorporated in slowly dissolving tablets made, for instance, of fat and wax substances or evenly distributed in a tablet of an insoluble substance such as a physiologically inert plastic substance.

In order to obtain dosage units of oral preparations—tablets, capsules, etc.—which are designed so as to prevent release of and possible decomposition of the active substance in the gastric juice, the tablets, dragees etc. may be enteric-coated, that is provided with a layer of gastric juice-resistant enteric film or coating having such properties that it is not dissolved at the acidic pH in the gastric juice. Thus, the active substance will not be released until the preparation reaches the intestines. As examples of such known enteric coatings may be mentioned cellulose acetate phthalate, hydroxypropyl-methylcellulose phthalates such as those sold under the trade names HP 55 and HP 50, and EDRAGIT®L and EUDRAGIT®S.

Liquid preparations for oral application may be in the form of elixirs, syrups or suspensions, for example solutions containing from about 0.1% to 20% by weight of active substance, sugar and a mixture of ethanol, water glycerol, propylene glycol and optionally aroma, saccharine and/or carboxymethylcellulose as a dispersing agent.

The term "purified" as used herein in reference to collagens denotes that the indicated molecules are present in the substantial absence of other biological macromolecules, e.g., polynucleotides, proteins, and the like. The term "purified" as used herein preferably means at least 95% by weight, more preferably at least 99.8% by weight, of the indicated biological macromolecules present (but water, buffers, and other small molecules, especially molecules having a molecular weight of less than 1000 daltons can be present). The term "isolated" as used herein refers to a protein molecule separated not only from other proteins that are present in the natural source of the protein, but also from other proteins, and preferably refers to a protein found in the presence of (if anything) only a solvent, buffer, ion, or other component normally present in a solution of the same. The terms "isolated" and "purified" do not encompass proteins present in their natural source.

EXAMPLES

The following examples are provided for the purpose of illustrating the subject invention and should not be considered as limiting the scope of the invention.

In Vivo Animal Study Regarding Development Of Antibodies To Collagen Following Immunization With Collagen Groups of 10 DBA/1 mice were immunized with either human type II collagen (CII), mammalian cell derived recombinant type II collagen (rCII+), or insect cell derived recombinant type II collagen (rCII−). In each case, the collagen was dissolved in 0.01M acetic acid and then emulsized in a 1 to 1 ratio with Complete Freud's Adjuvant prior to immunization. Each mouse received 100 μg of protein subcutaneously in the tail. Two groups received two doses of 100 μg rCII+ or rCII−, thereby receiving in total 200 μg of rCII+ or rCII−. In cases where 200 μg total dose was administered, the first 100 μg dose of protein was administered as described above. The second 100 μg dose of protein was emulsified in incomplete Freud's adjuvent and administered three weeks after administration of the first dose.

The incidence of arthritis was measured and reported, as set forth in Table 2, at six weeks (following immunization).

TABLE 2

| Antigen Used for Immunization | % Arthritic Mice | Antibodies to HII |
| --- | --- | --- |
| rCII + (100 μg) | 4/10 | 39 ± 19 |
| rCII + (200 μg) | 9/10 | 120.8 ± 40 |
| rCII − (100 μg) | 8/10 | 69.3 ± 39 |
| rCII − (200 μg) | 9/10 | 80.3 ± 39 |
| CII (100 μg) | 9/10 | 117.5 ± 56 |

As evidenced by the data set forth in Table 2, antibodies represent the mean levels/group (expressed in units) against native human type II collagen (HII) sera collected four weeks after immunization.

In Vivo Animal Study Regarding Development Of Antibodies To Collagen Following Intravenous Administration Of Collagen Ovalalbumin, human type II collagen (CII), mammalian cell derived recombinant type II collagen (rCII+), or insect cell derived recombinant type II collagen (rCII−) were administered intravenously to groups of 10 DBA/1 mice. The collagens (CII, rCII+ and rCII−) were dissolved in 0.01M acetic acid and dialyzed against PBS prior to administration. Either 33 μg or 333 μg of protein was administered daily for three days such that a total of either 100 μg or 1000 μg of protein was administered to each test mouse. Four days after administration of the last dose, the mice were then immunized with CII. The incidence of arthritis at six (6) weeks after immunization is set forth at Table 3.

TABLE 3

| Antigen Administered Intravenously | % Arthritic Mice | Antibodies to HII |
| --- | --- | --- |
| OVA (1000 μg) | 9/10 | 100.8 ± 40 |
| rCII + (1000 μg) | 0/10 | 120 ± 5.3 p ≦ 0.0005 |
| rCII + (100 μg) | 0/10 | 14.3 ± 6 p ≦ 0.0005 |
| rCII − (1000 μg) | 0/10 | 14.9 ± 7 p ≦ 0.0005 |
| rCII − (100 μg) | 0/10 | 8.5 ± 4 p ≦ 0.0005 |
| CII (1000 μg) | 0/10 | 5.5 ± 1 p ≦ 0.0005 |

Antibodies represent the mean levels/group (expressed in units) against native human type II collagen (HII) using sera collected four (4) weeks after immunization. The statistics are reported using Student's T test.

In Vivo Animal Study Regarding Development Of Antibodies To Collagen Following Oral Administration Of Collagen Groups of ten to twelve DBA/1 mice were orally administered either Ovalbumin, human type II collagen (CII), mammalian cell derived recombinant type II collagen (rCII+), or insect cell derived recombinant type II collagen (rCII−). The collagens were dissolved in 0.01M acetic acid and administered four (4) times per week for two weeks for a total of eight doses. Either 10 μg or 100 μg was administered daily so that mice received a total of either 80 μg or 800 μg of protein. Three (3) days after receipt of the last dose, the mice were then immunized with CII. Table 4 provides the incidence of arthritis at five weeks after immunization.

TABLE 4

| Antigen Fed | % Arthritic Mice | Antibodies to HII |
| --- | --- | --- |
| OVA (800 μg) | 8/12 (67%) | 100.3 ± 48 |
| rCII + (800 μg) | 8/12 (67%) | 53 ± 33 p ≦ .01 |
| rCII + (80 μg) | 2/10 (20%) p ≦ 0.05 | 45 ± 45 p ≦ .01 |
| rCII − (1000 μg) | 8/12 (67%) | 91 ± 77 |
| rCII − (100 μg) | 3/12 (25%) p ≦ 0.95 | 63 ± 24 p ≦ .025 |
| CII (1000 μg) | 6/12 (50%) | 47 ± 23 p ≦ .025 |

The reported statistical variance was calculated using a Fisher's Exact Test. Antibodies represent the mean levels per group (expressed in units) against native human type II collagen (HII) using sera collected four weeks after immunization. Statistics are reported using Student's T test.

Human Platelet Aggregation Study

Type III recombinant collagen and human types I and III collagen were tested in blood samples from four donors and tested, using routine platelet aggregation assays. All types of collagen demonstrated platelet aggregation activity. More specifically, the percentage of aggregation of 10 μg of recombinant type III collagen is equivalent to the percent aggregation of either 0.3 μg of type III collagen or 0.6 μg of type I collagen.

INCORPORATION BY REFERENCE

All patents, patents applications, and publications cited are incorporated herein by reference.

EQUIVALENTS

The foregoing written specification is considered to be sufficient to enable one skilled in the art to practice the invention. Indeed, various modifications of the above-described invention which are obvious to those skilled in the fields of immunology, biochemistry, or related fields are intended to be within the scope of the following claims.

What is claimed is:

1. A compound comprising:
   a collagen molecule component chemically cross-linked to a mucosa binding molecule component, wherein said compound is useful for the treatment of an arthritis.
2. The compound of claim 1, wherein the collagen molecule is selected from the group consisting of type II collagen, type IX collagen, and type XI collagen.
3. The compound of claim 1, wherein the collagen molecule is a type II collagen derivative.
4. The compound of claim 3, wherein the collagen derivative is variably glycosylated.
5. The compound of claim 1, where the mucosa binding molecule is selected from the group consisting of mucosa binding molecules derived from mucosa binding structures of bacterial toxins, bacterial fimbriae, viral attachment proteins, and plant lectins.
6. The compound of claim 5, wherein the mucosa binding molecule can bind to ganglioside $GM_1$.
7. The compound of claim 5, wherein the mucosa binding molecule is the subunit of cholera toxin or heat-labile enterotoxin of *E. coli*.
8. A method of treating arthritis, said method comprising the step of administering an effective amount of a compound according to claim 1.
9. The method of claim 8, wherein the collagen molecule is selected from the group consisting of type II collagen, type IX collagen, and type XI collagen.
10. The method of claim 9, wherein the collagen molecule is a type II collagen derivative.
11. The method of claim 10, wherein the collagen derivative is variably glycosylated.
12. The method of claim 8, where the mucosa binding molecule is selected from the group consisting of mucosa binding molecules derived from mucosa binding structures of bacterial toxins, bacterial fimbriae, viral attachment proteins, and plant lectins.
13. The method of claim 12, wherein the mucosa binding protein can bind to ganglioside $GM_1$.
14. The method of claim 12, wherein the mucosa binding molecule is the β subunit of cholera toxin or heat-labile enterotoxin of *E. coli*.

* * * * *